United States Patent [19]
Higuchi

[11] Patent Number: 5,090,411
[45] Date of Patent: Feb. 25, 1992

[54] ULTRASONIC DIAGNOSIS APPARATUS
[75] Inventor: Jirou Higuchi, Ootawara, Japan
[73] Assignee: Kabushiki Kaisha Toshiba, Kawasaki, Japan
[21] Appl. No.: 647,231
[22] Filed: Jan. 29, 1991
[30] Foreign Application Priority Data
  Jan. 31, 1990 [JP]  Japan ............................ 2-18925
[51] Int. Cl.⁵ ................................................ A61B 8/00
[52] U.S. Cl. ..................... 128/660.05; 128/661.08; 128/660.04
[58] Field of Search ................ 128/660.01, 660.04, 128/660.05, 661.07, 661.08, 662.02

[56] References Cited
U.S. PATENT DOCUMENTS

| | | | |
|---|---|---|---|
| 4,346,717 | 8/1982 | Haerten | 128/662.05 |
| 4,416,286 | 11/1983 | Iinuma et al. | 128/660.05 |
| 4,501,277 | 2/1985 | Hongo | 128/660.05 |
| 4,773,425 | 9/1988 | Saitou | 128/660.04 |

Primary Examiner—Francis Jaworski
Assistant Examiner—George Manuel
Attorney, Agent, or Firm—Finnegan, Henderson, Farabow, Garrett, and Dunner

[57] ABSTRACT

An ultrasonic diagnosis apparatus in which ultrasonic waves transmitted to a subject under examination and reflected from a subject under examination are received to generate ultrasonic images such as a B-mode image (tomographic image) and a D-mode image indicating a blood-flow velocity profile and a superimposed image in which a marker is superimposed upon, for example, the B-mode image in a movable fashion is displayed. When the superimposed image is displayed, the brightness of the marker is controlled such that the brightness of the marker is changed when the position of the marker is changed and the brightness of the marker is restored after a predetermined period of time has elapsed.

7 Claims, 9 Drawing Sheets

F I G. 10 ated by said superimposing means, in which said character is superimposed on said B-mode image or said BDF-mode image and a M-mode image and/or a D-mode image for said specific portion of said subject under examination; and

ULTRASONIC DIAGNOSIS APPARATUS

BACKGROUND OF THE INVENTION

1. Field of the Invention

The present invention relates to an ultrasonic diagnosis apparatus which permits various types of ultrasonic diagnostic images of a subject under examination, such as a B-mode image (a tomographic image), an M (motion)-mode image, a D-mode image (which is also called a one-point Doppler image or an FFT doppler image), a BDF-mode image (an image in which a CFM (color flow mapping) image is superimposed on a B-mode image), an MDF-mode image (an image in which a CFM image is superimposed on an M-mode image, etc., to be displayed individually or in combination.

2. Description of the Related Art

Figure 1:
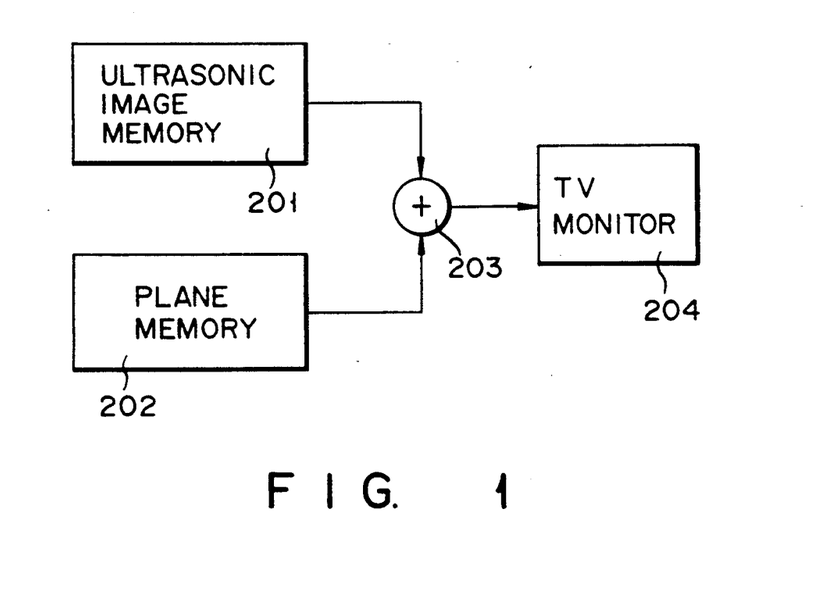
FIG. 1 is a schematic block diagram of a display system of a conventional ultrasonic diagnosis apparatus.

In recent ultrasonic diagnosis apparatuses, auxiliary information required for diagnosis is sometimes added to ultrasonic images such as a B-mode image, a D-mode image, an M-mode image, a BDF-mode image, an MDF-mode image, etc. By way of example, a marker indicating the position of a sampling point at which data is acquired to produce a D-mode image is superimposed on a B-mode image or a BDF-mode image. This will be described with reference to FIG. 1. That is, an ultrasonic image memory 201 for storing an ultrasonic image such as a B-mode image or a BDF-mode image, a plane memory 202 for storing auxiliary information such as a marker or a character and a mixer 203 for mixing information from these memories to produce a superimposition image are provided. Whereby, the marker and the ultrasonic image can be displayed simultaneously on a TV monitor 204.

Figure 2:
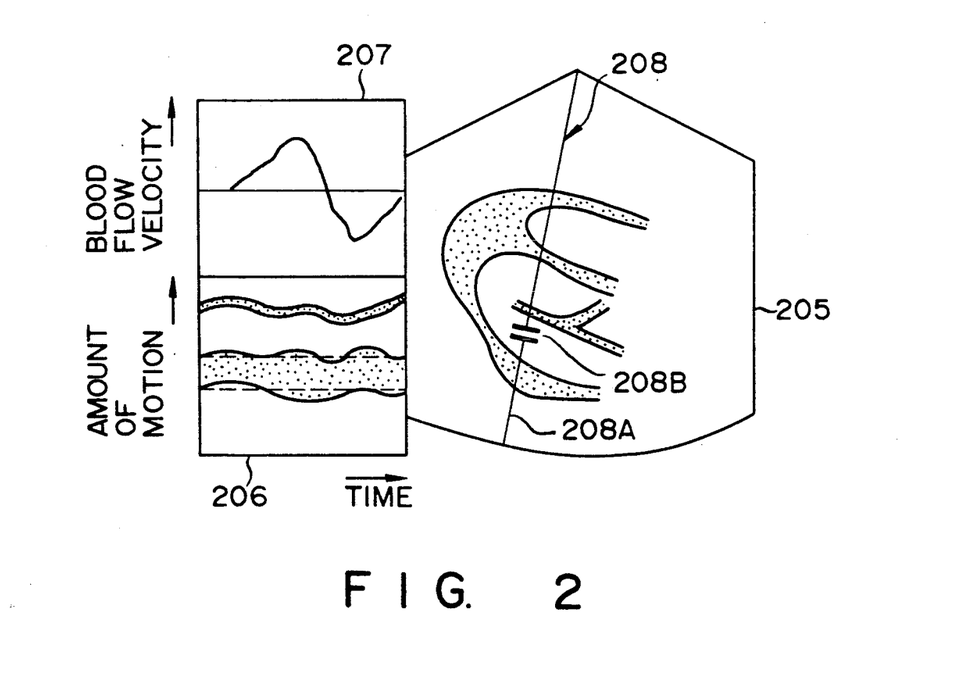
FIG. 2 illustrates one example of an ultrasonic image display format on a TV monitor of a conventional ultrasonic diagnosis apparatus.

FIG. 2 illustrates a display example in which an ultrasonic image and a marker are displayed simultaneously on the TV monitor 204. In this example, a sector-scan B-mode image 205 is displayed at the right of the screen of the TV monitor 204, and an M-mode image and a D-mode image are displayed at the lower left and the upper left, respectively, of the screen of the TV monitor 204 as shown. The M-mode image indicates variations of a part of the body of a subject under examination that corresponds to the marker 208 set on the B-mode image with time. The marker 208 is comprised of a line marker 208A and a position marker 208B which indicates the position of a sampling point set on the line marker 208A. The D-mode image 207 indicates a profile of blood flow velocity in the position of the subject corresponding to the position marker 208B. If the marker 208 is displayed simultaneously with the B-mode image 205 in this way, an operator, such as a doctor, is able to learn where the sampling point is positioned on the B-mode image. This is very helpful to diagnosis.

With such a conventional marker display, however, if the operator adjusts the brightness of the marker 208 for easier viewing when setting the position of the sampling point, the marker 208 will be an obstacle to observation of the B-mode image. If, on the other hand, the marker is adjusted so that it is not an obstacle to observation of the B-mode image, the operator will have difficulty in finding the position of the marker 208.

SUMMARY OF THE INVENTION

It is therefore an object of the present invention to provide an ultrasonic diagnosis apparatus which permits a marker indicating the position of a sampling point to be adjusted for easy viewing only when necessary and thereby improves the accuracy of ultrasonic diagnosis.

According to an aspect of the present invention there is provided an ultrasonic diagnosis apparatus comprising:

ultrasonic image generating mean for transmitting ultrasonic waves to and receiving reflected ultrasonic waves from a subject under examination to produce a plurality of ultrasonic images;

superimposing means for superimposing auxiliary information previously prepared on at least one of said ultrasonic images to produce a superimposition image;

display means for displaying said superimposition image produced by said superimposing means and/or at least one of said ultrasonic images; and control means for controlling a visible effect of said auxiliary information on said ultrasonic image on which said auxiliary information is superimposed when said superimposition image is displayed by said display means.

According to another aspect of the present invention there is provided an ultrasonic diagnosis apparatus comprising:

ultrasonic image generating means for transmitting ultrasonic waves to and receiving reflected ultrasonic waves from a subject under examination to generate a B-mode image, an M-mode image, a D-mode image, a BDF-mode image and/or an MDF-mode image;

superimposing means for superimposing a marker upon said B-mode image or said BDF-mode image in a movable fashion to indicate a specific portion of said subject under examination;

display means for displaying a superimposition image, obtained by said superimposition means, in which said marker is superimposed on said B-mode image or said BDF-mode image and a M-mode image and/or a D-mode image for said specific portion of said subject under examination specified by said marker; and control means for controlling the brightness of said marker when said superimposition image is displayed by said display means such that said marker changes its brightness in response to a change of said marker in position and restores its brightness after the elapse of a predetermined period of time.

According to still another aspect of the present invention there is provided an ultrasonic diagnosis apparatus comprising:

ultrasonic image generating means for transmitting ultrasonic waves to and receiving reflected ultrasonic waves from a subject under examination to generate a B-mode image, an M-mode image, a D-mode image, a BDF-mode image and/or an MDF-mode image;

superimposing means for superimposing a character upon said B-mode image or said BDF-mode image with its position fixed to indicate an ultrasonic diagnosis condition previously prepared;

display means for displaying a superimposition image, obtained by said superimposition means, in which said character is superimposed on said B-mode image or said BDF-mode image and a M-mode image and/or a D-mode image for said specific portion of said subject under examination; and control means for controlling the brightness of said character when said superimposition image is displayed by said display means such that said character changes its brightness in response to a shutter operation of an instant camera disposed in the neighborhood of said display means and restores its brightness after the elapse of a predetermined period of time.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

An ultrasonic diagnosis apparatus according to an embodiment of the present invention will be described below.

Figure 3:
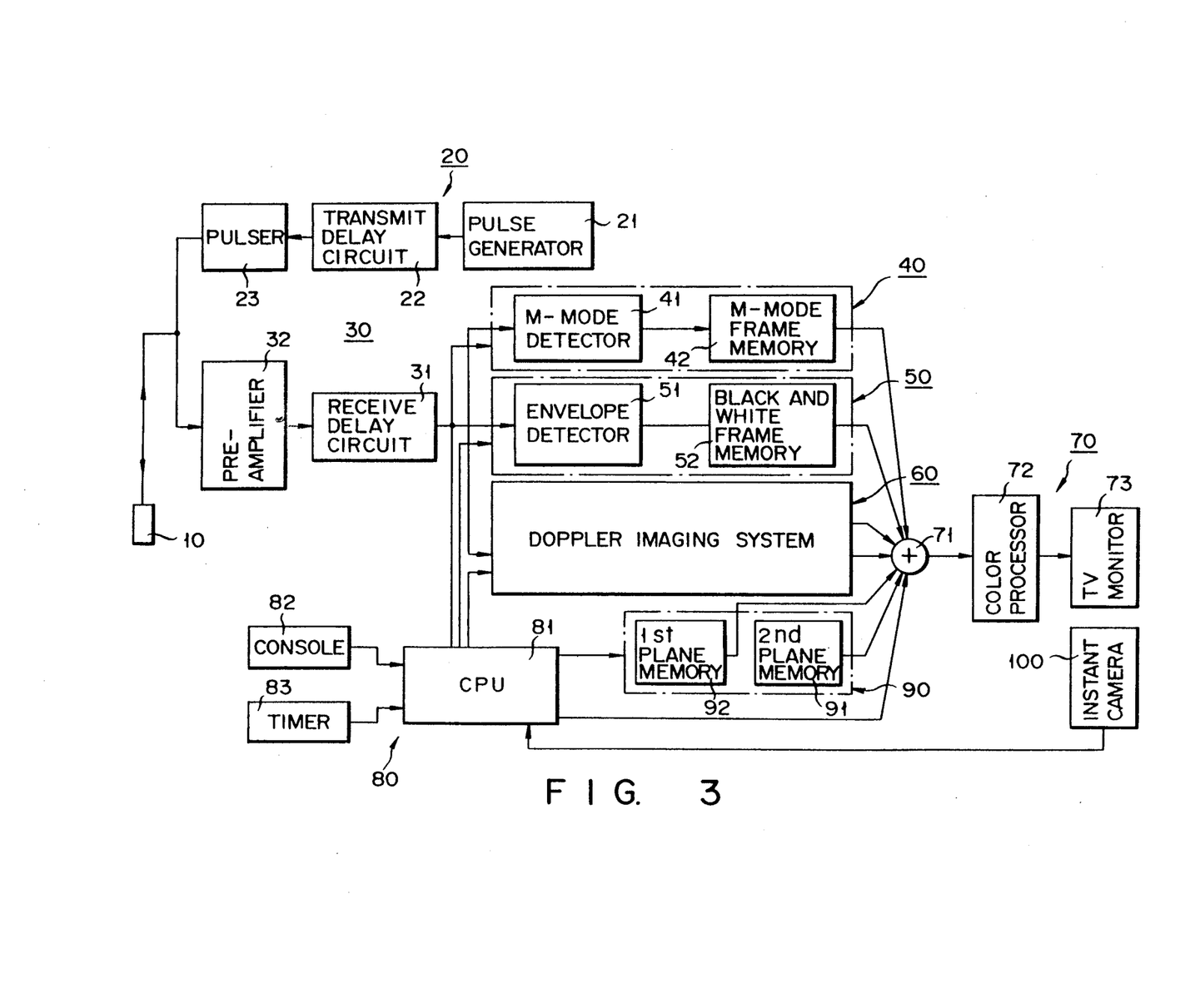
FIG. 3 is a block diagram of an ultrasonic diagnosis apparatus embodying the present invention.
Figure 4:
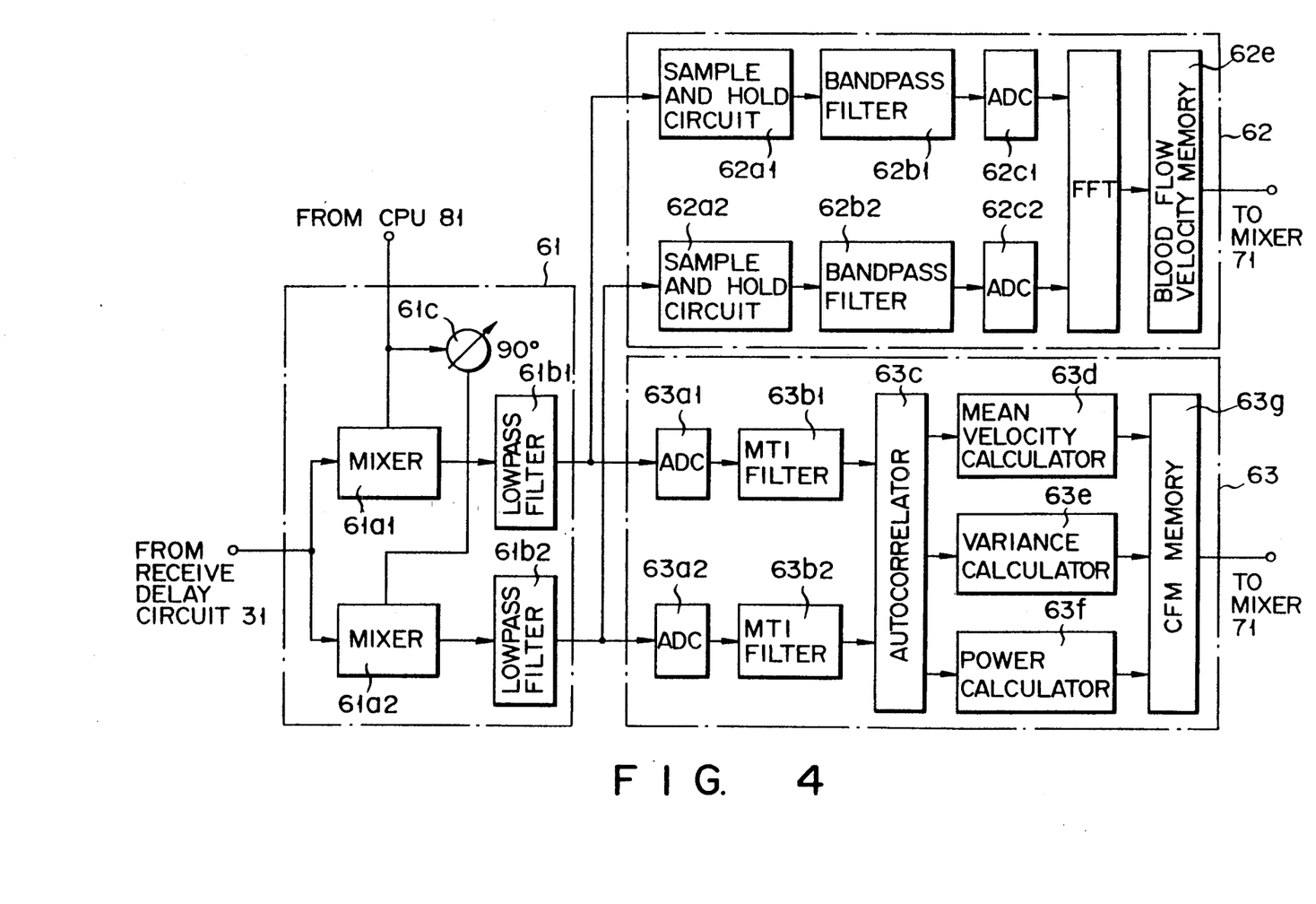
FIG. 4 is a detailed block diagram of the Doppler processing system of FIG. 3.
Figure 5:
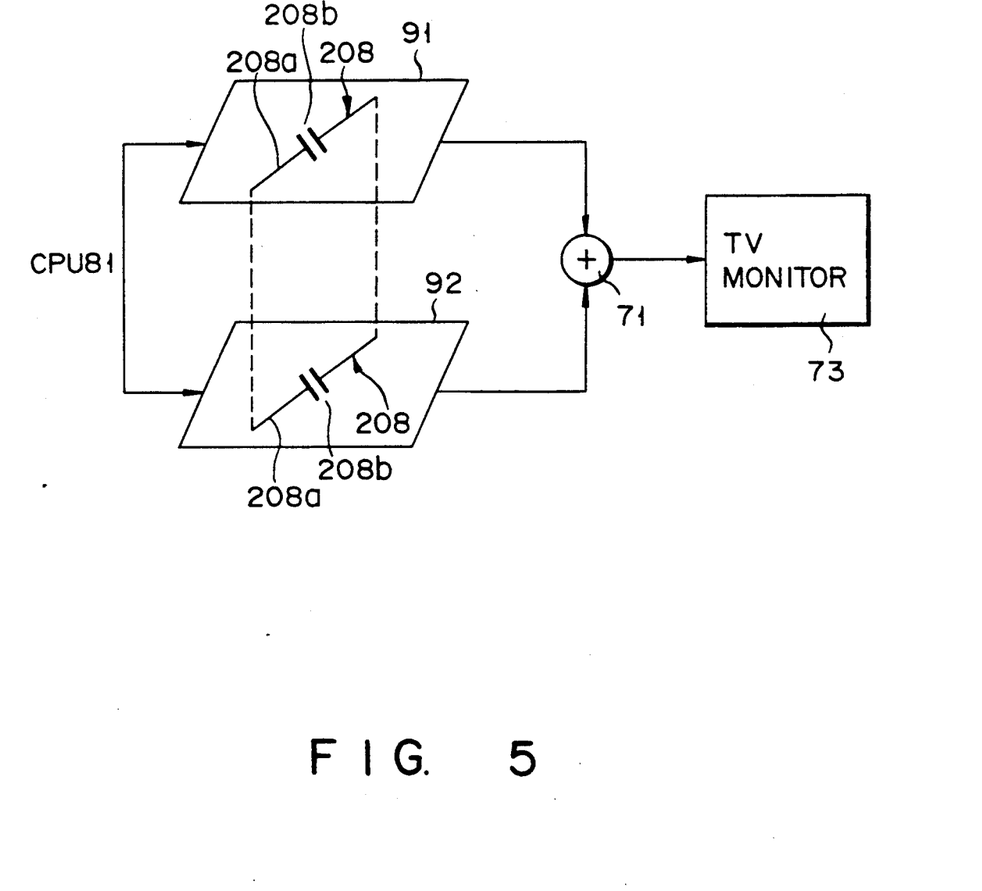
FIG. 5 is a schematic block diagram of a first display system for use with the ultrasonic diagnosis apparatus of FIG. 3.

FIG. 3 is a block diagram of the ultrasonic diagnosis apparatus embodying the present invention, FIG. 4 is a detailed block diagram of the Doppler processing system of FIG. 3 and FIG. 5 is a schematic block diagram of a first display system of the ultrasonic diagnosis apparatus of FIG. 3.

As illustrated in FIG. 3, the ultrasonic diagnosis apparatus of the present embodiment is constructed from an ultrasonic probe 10, a transmitting system 20, a receiving system 30, an M-mode image producing system 40, a B-mode image producing system 50, a Doppler image producing system 60, a display system 70, a control system 80 and an auxiliary information system 90. An instant camera 100 is disposed in the neighborhood of the display system 70. The ultrasonic probe 10, the transmitting system 20, the receiving system 30, the M-mode image producing system 40, the B-mode image producing system 50 and the Doppler image producing system 60 serve as a system for transmitting ultrasonic waves to and receiving reflected ultrasonic waves from a subject under examination (not shown) to produce a B mode image, an M-mode image, a D-mode image, a BDF-mode image and/or an MDF-mode image of the subject under examination. A configuration of the auxiliary information system 90 only is illustrated in FIG. 5.

The ultrasonic probe of FIG. 3 can be an electronic sector scanning type probe in which a large number of small ultrasonic transducers are juxtaposed. In this embodiment, the ultrasonic probe of FIG. 3 will be an electric linear scanning type probe or an electric convex linear scanning type probe.

The transmitting system 20 is comprised of a pulse generator 21, a transmit delay circuit 22 and a pulser 23, and is adapted to vary the foci of transmitted ultrasonic beams and the timing of exciting of each of the transducers in accordance with beam deflection angles when the ultrasonic beams are transmitted. As a result, the directions of transmission of the ultrasonic beams from the ultrasonic probe 10 are sequentially changed so as to scan a sector, thereby performing an electronic sector scan.

The receiving system 30 is comprised of a preamplifier 32 and a receive delay circuit 31, and is adapted to vary the timing of signal reception of each of the transducers of the ultrasonic probe 10, in accordance with the focusing and beam deflection, when reflected ultrasonic beams are received.

The M-mode image producing system 40 is comprised of an M-mode detector 41 and an M-mode frame memory 42, and is adapted to produce an M-mode image.

The B-mode image producing system 50 is comprised of an envelope detector 51 and a black and white frame memory 52, and is adapted to produce a B-mode image.

The Doppler image producing system 60 is adapted, as shown in FIG. 4, to produce a D-mode image and CFM data. The CFM data is superimposed on a B-mode image to produce a BDF-mode image. Also, the CFM data is superimposed on an M-mode image to produce an Mdf-mode image. More specifically, the Doppler image producing system 60 comprises a 90° phase detector 61, a D-mode image producing system 62 and a CFM data producing system 63.

The 90° phase detector 61 is constructed from two mixers 61a1 and 61a2, two lowpass filters 61b1 and 61b2 and a phase shifter 61c which receives a standard signal from a CPU 81, which will be described later, in the control system 80, and provides the mixers 61a1 and 61a2 with reference signals having 90-degree phase difference. The mixers 61a1 and 61a2 receive a received signal from the receive delay circuit 31, and the lowpass filters 61b1 and 61b2 provide two detector outputs.

The D-mode image producing system 62 comprises two sample and hold circuits 62a1 and 62a2 which receive the detector outputs of the lowpass filters 61b1 and 61b2, respectively, of the 90° phase shifter, two bandpass filters 62b1 and 62b2 coupled to the sample and hold circuits 62a1 and 62a2, respectively, two analog-to-digital converters (ADCs) 62c1 and 62c2 coupled to the bandpass filters 62b1 and 62b2, respectively, a fast Fourier transformer (FFT) 62d coupled to the ADCs 62c1 and 62c2 and a blood flow memory 62e for storing blood flow data obtained by the FFT 62d. The blood flow data stored in the blood flow memory 62e is sent to a mixer 71, which will be described later, of the imaging system 70.

The CFM data producing system 63 comprises two ADCs 63a1 and 63a2 connected to receive the detector outputs of the lowpass filters 61b1 and 61b2, respectively, of the 90° phase detector 61, two moving target indicator (MTI) filters 63b1 and 63b2 coupled to the ADCs 63a1 and 63a2, respectively, an autocorrelator 63c receiving outputs of the MTI filters 63b1 and 63b2, a mean velocity calculator 63d coupled to the autocorrelator 63e, a variance calculator 63c coupled to the autocorrelator 63c, a power calculator 63f coupled to the autocorrelator 63c, and a CFM memory 63g for storing CFM data output from the mean velocity calculator 63d, the variance calculator 63c and the power calculator 63f. The CFM data stored in the CFM memory 62g is sent to the mixer 71 of the imaging system 70.

Figure 6A:
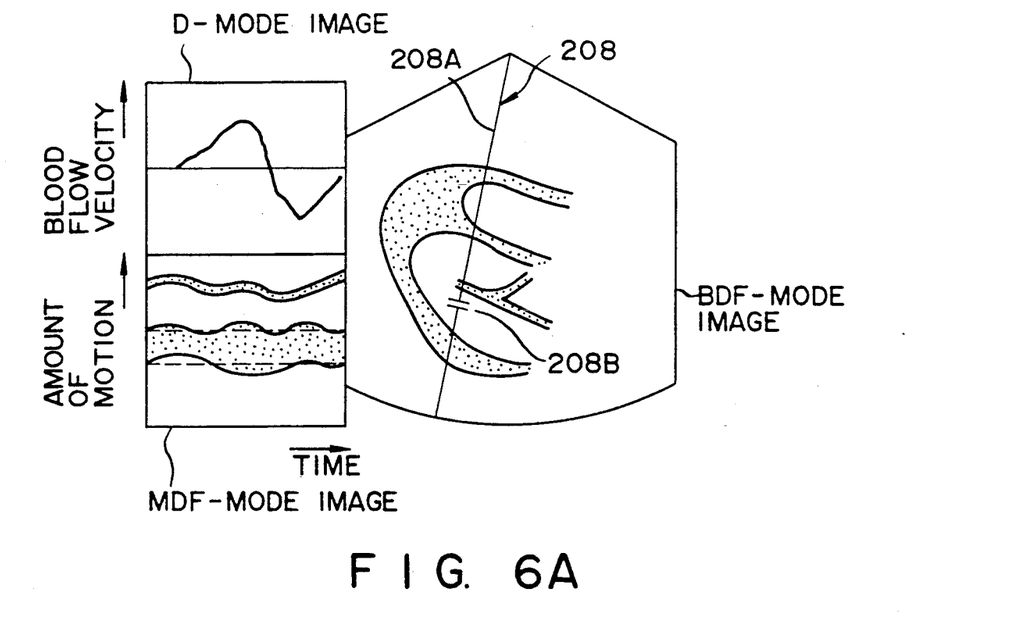
FIG. 6A illustrates an ultrasonic image display format prior a change in the first display system.

Returning to FIG. 3, the imaging system 70 comprises the mixer 71, a color processor 72 and a TV monitor 73. The imaging system 70 mixes ultrasonic images from the M-mode image producing system 40, the B-mode image producing system 50, the Doppler image producing system 60 and marker data or character data, that is, auxiliary information from the auxiliary information system 90 to produce a superimposed image which is displayed on the TV monitor 73. In this case, superimposed-image display formats include a two-image display format in which a B-mode image on which a marker is superimposed and an M-mode image are displayed simultaneously, a three-image display format in which a marker-superimposed B-mode image, an M-mode image and a D-mode image are displayed simultaneously, a two-image display format in which a marker-superimposed BDF-mode image and an MDF-mode image are displayed simultaneously and a three-image display format in which a marker-superimposed BDF-mode image, an MDF-mode image and a D-mode image are displayed simultaneously. FIG. 6A illustrates a typical display example of the three-image display format of a marker-superimposed BDF-mode image, an MDF-mode image and a D-mode image. A marker 208 of FIG. 6A is comprised of a line marker 208A and a position marker 208B, the line marker indicating a detection line of the M-mode image and the position marker indicating a detection point (a sampling point) of the D-mode image.

Returning to FIG. 3, the control system 80 is constructed from the CPU 81, a console 82 equipped with a trackball or a joystick and a timer 83, and is adapted to allow an operator to set ultrasonic diagnostic conditions and to choose ultrasonic images to be displayed, control a display format of auxiliary information and serve as a system controller.

Figure 6B:
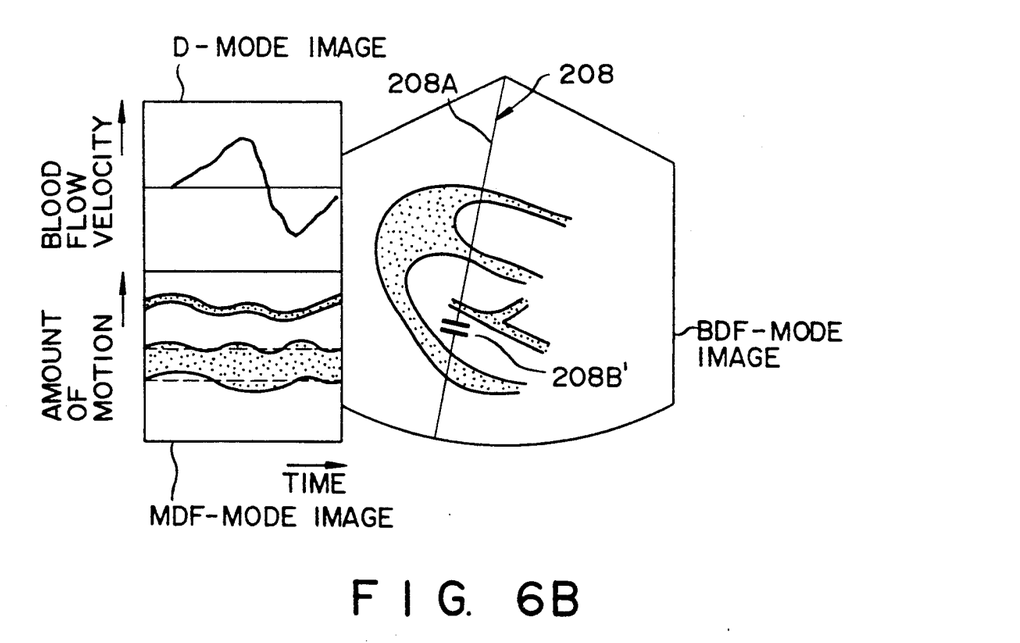
FIG. 6B illustrates an ultrasonic image display format after the change in the first display system.

The auxiliary information system 90 is provided, as illustrated in FIG. 5, with a first plane memory 91 and a second plane memory 92, each of which stores auxiliary information such as marker data or character data, and is coupled to the TV monitor 73 via the mixer 71. Under the control of the CPU 81 only the first plane memory 91 is coupled to the TV monitor, or, both of the first and second plane memories are coupled to the TV monitor. This is referred to as plane addition and subtraction control. Assuming that auxiliary information represents the marker 208, plane addition and subtraction control is performed such that the brightness of the marker 208 is decreased, as shown in FIG. 6A, when only the first plane memory 91 is coupled to the TV monitor 73 and, on the other hand, the brightness of the marker is increased, as shown in FIG. 6B, when the first and second plane memories 91 and 92 are both coupled to the TV monitor 73 via the mixer 71. The reason is that the former is a display of one plane and the latter is a display of two planes. States in which such a change of brightness of the marker occurs will be described later.

When the shutter of the instant camera 100 is released (when its shutter switch is turned on), a shutter signal is transmitted to the CPU 81 to perform plane addition and subtraction control of the auxiliary information system 90.

The ultrasonic diagnosis apparatus of the present embodiment, constructed as above, operates as follows. The ultrasonic probe 10 is driven by the transmit system 20 and the receive system 30 to transmit ultrasonic beams to a subject under examination (not shown) for electronic sector scanning thereof. The ultrasonic beams are transmitted by ultrasonic transducers to the subject and are reflected from organs such as heart walls, blood vessel walls and blood flow (chiefly red blood cells) within blood vessels of the subject, and resulting echo signals are received by the ultrasonic transducers. The receiving system 30 outputs ultrasonic received signals in analog form.

The B-mode imaging system 50 detects an envelope of the ultrasonic received signals by the use of the envelope detector 51 and delivers resulting B-mode image data (tomographic image information) to the black and white frame memory 52. The M-mode imaging system 40 detects variations of motion with time on a specific raster (the line marker 208A) in the sector scan and delivers resulting M-mode image data to the M-mode frame memory 42. The specific raster on which the M-mode image data is detected is determined by the line marker 208A set on the B-mode image. The D-mode imaging system 62 in the Doppler imaging system 60 detects blood flow velocity at a specific point (sampling point) on the sam specific raster (line marker 208A) as in the case of the M-mode image detection and delivers resulting blood flow data to the blood flow velocity memory 62e. The DF-mode imaging system 63 in the Doppler imaging system 60 detects CFM data represented by the mean velocity, variance and power of blood flow in all rasters for a sector scan as in the case of B-mode image detection and delivers resulting CFM data to the CFM memory 62g.

The mixer 71 mixes the B mode image data from the black and white frame memory 52, the M-mode image data from the M-mode frame memory 42, the D-mode image data from the blood flow velocity memory 62e, the CFM data from the CFM memory 63g and the marker data from the auxiliary information system 90. Consequently, a superimposed image comprised of the BDF-mode ultrasonic image, the MDF-mode ultrasonic image, the D-mode ultrasonic image and the marker 208 is displayed on the TV monitor 73 as shown in FIG. 6A.

The following is a description of the states in which the brightness of the marker 208 is changed. The state of FIGS. 7 and 8, in which the marker 208 is moved, is referred to as a first display system, while the state of FIGS. 9 and 10, in which the shutter switch of the instant camera 100 is turned on, is referred to as a second display system, which will be described below in detail.

Figure 7:
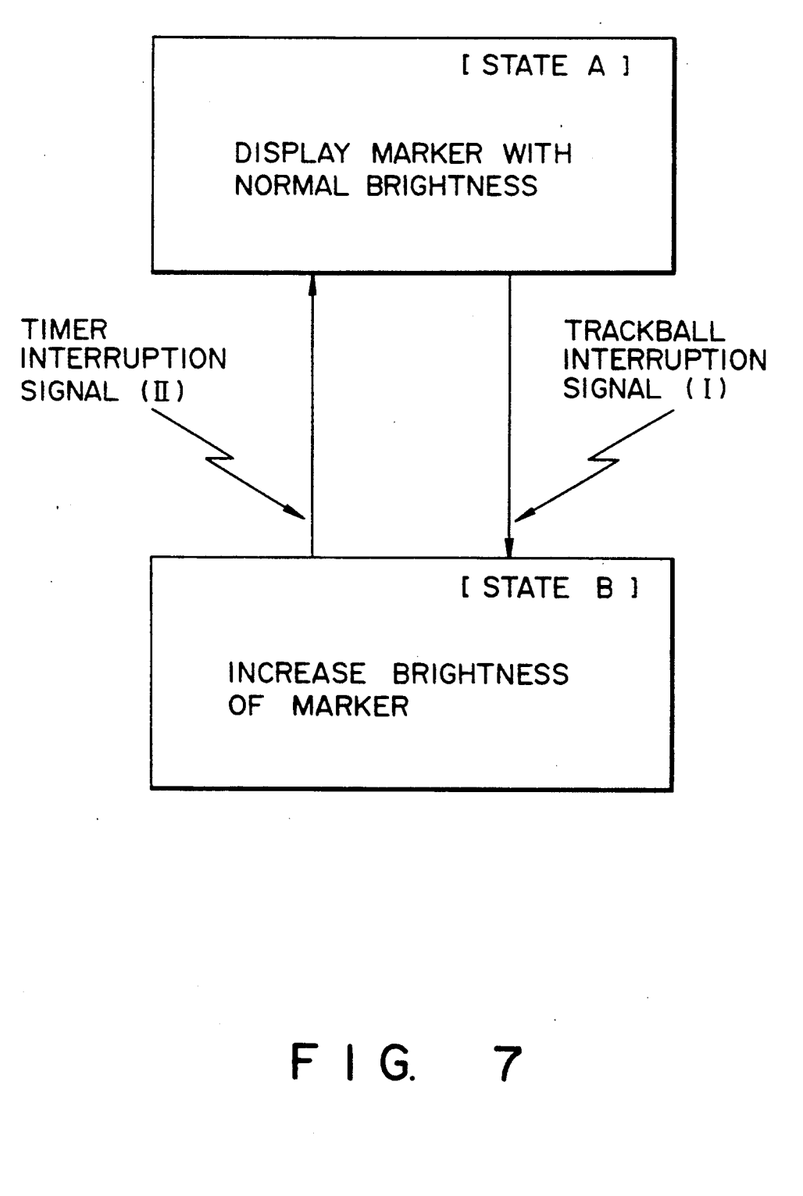
FIG. 7 illustrates a change of state in the first display system.

The transition states of in the first display system are shown in FIG. 7. By operating the console 82 to start the auxiliary information system 90, a superimposed image comprised of a BDF-mode ultrasonic image, an MDF-mode ultrasonic image, a D-mode ultrasonic image and marker 208 is displayed on the TV monitor 73 as shown in FIG. 6A. This state is referred to as state A. In state A, the marker 208 is displayed with a normal brightness, i.e., the marker is displayed with one plane. When the trackball on the console 82 is operated to move the marker 208, a trackball interruption signal (I) is fed into the CPU 81 so that a transition from state A to state B occurs. In state B, the brightness of the marker 208 is increased, i.e., the marker is displayed with two planes. When the transition from state A to state B occurs, the timer 83 is started. When a predetermined period of time elapses, a timer interruption signal (II) is fed into the CPU 81 so that the state returns to state A. Further, the timer 83 is cleared when the CPU 81 received the timer interruption signal (II).

Figure 8:
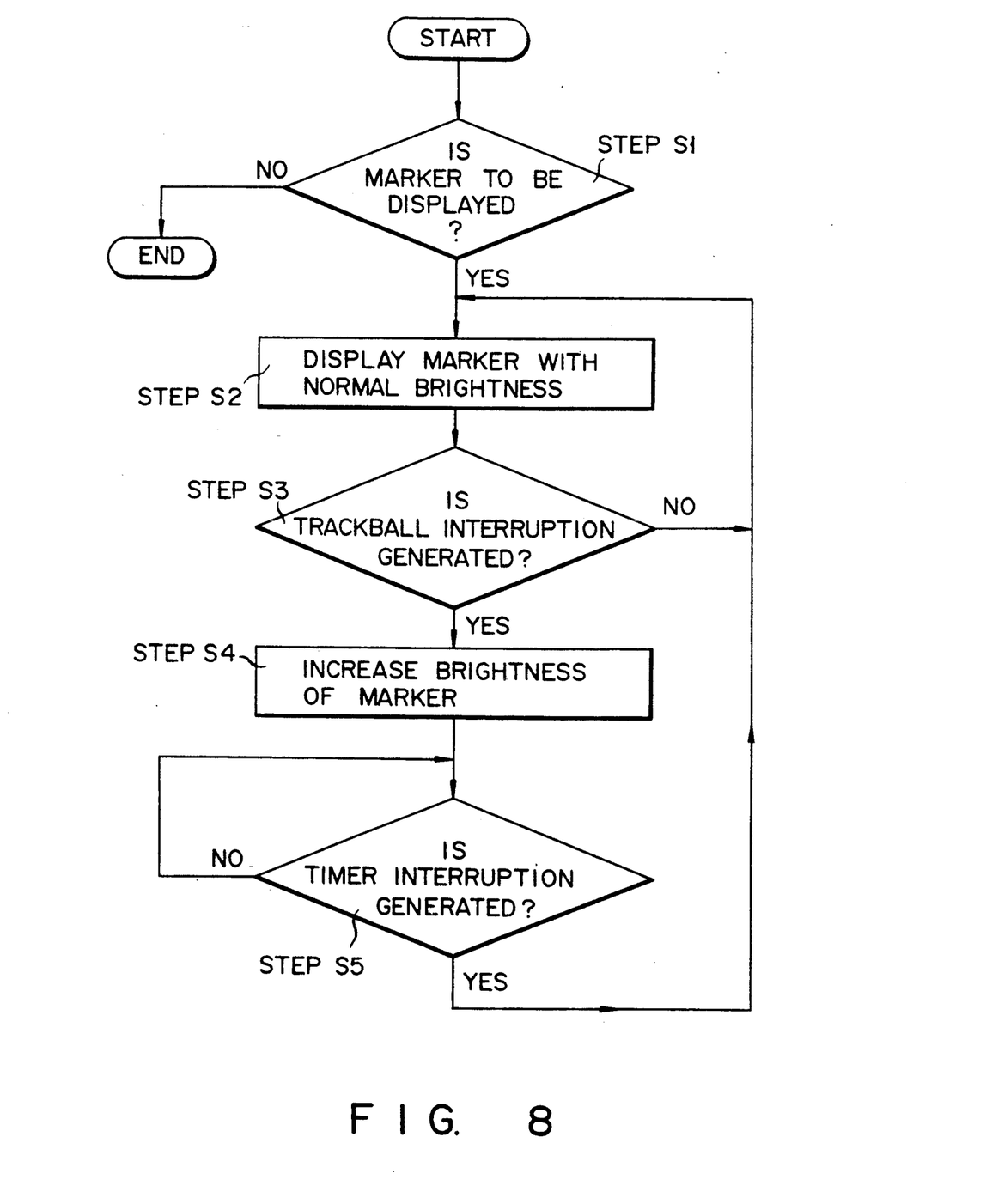
FIG. 8 is a flowchart illustrating the change of state in the first display system in detail.

The above state transistion will be understood more clearly by referring to FIG. 8. As shown, a decision is made, in step S1, as to whether or not the marker 208 is to be displayed. If not, the operation is terminated. If, on the other hand, the marker is to be displayed, the operation advances to step S2, whereby the marker is displayed in state A, that is, displayed a normal brightness. In step S3, when no trackball interruption is generated, state A is maintained. When a trackball interruption is generated, the state transition from state A to state B occurs so that the brightness of the marker is increased in step S4. In step S5, a decision is made as to whether or not a timer interruption is generated. If not, state B is maintained. When the timer interruption is generated, the state transition from state B to state A occurs.

That is, when marker is not moved (when the positioning of the sampling point is performed), the marker 208 is displayed with its brightness decreased as shown in FIG. 6A so that observation of ultrasonic images is only slightly affected. On the other hand, when the marker is moved (when positioning of the sampling point is not performed), the marker 208' is displayed with its brightness increased as shown in FIG. 6B. This is very useful in avoiding diagnostic errors and in improving the accuracy of diagnosis.

Figure 9:
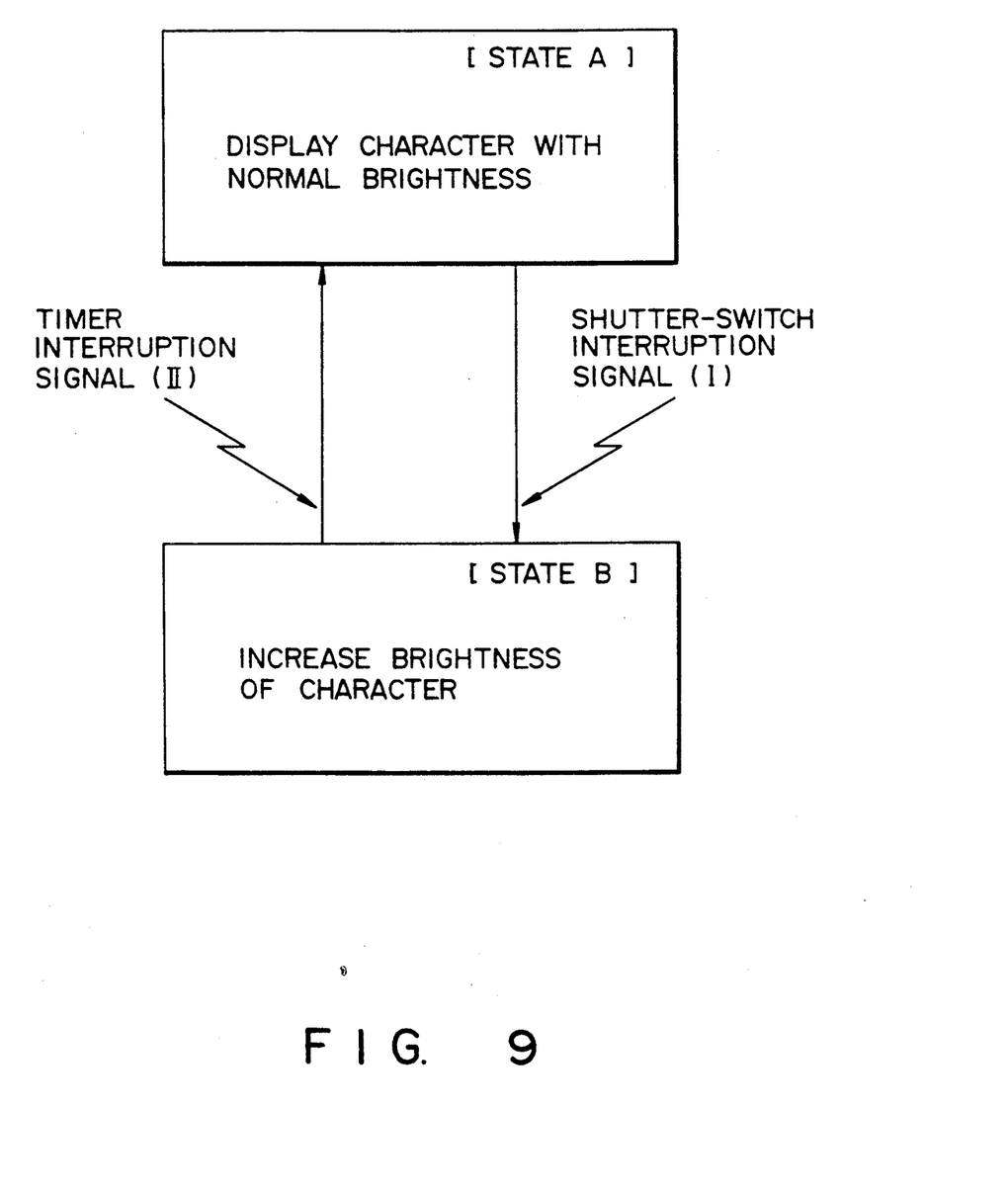
FIG. 9 illustrates a change of state in a second display system.

The transition states of the second display system are illustrated in FIG. 9. By operating the console 82 to start the auxiliary information system 90, the superimposed image comprised of the BDF-mode ultrasonic image, the MDF-mode ultrasonic image, the D-mode ultrasonic image and the marker 208 is displayed on the TV monitor 73 as shown in FIG. 6A. This state is referred to as state A. In state A, the marker 208 is displayed with a normal brightness, i.e., the marker is displayed with one plane. When the shutter switch of the instant camera 100 is turned on, a shutter-switch interruption signal (I) is fed into the CPU 81 so that a transition from state A to state B occurs. In state B, the brightness of the marker 208 is increased. Namely, the marker is displayed with two planes. When the state transition from state A to state B occurs the timer 83 is started. When a predetermined period of time elapses, a timer interruption signal (II) is fed into the CPU 81 so that the state transition from state B to state A occurs.

Figure 10:
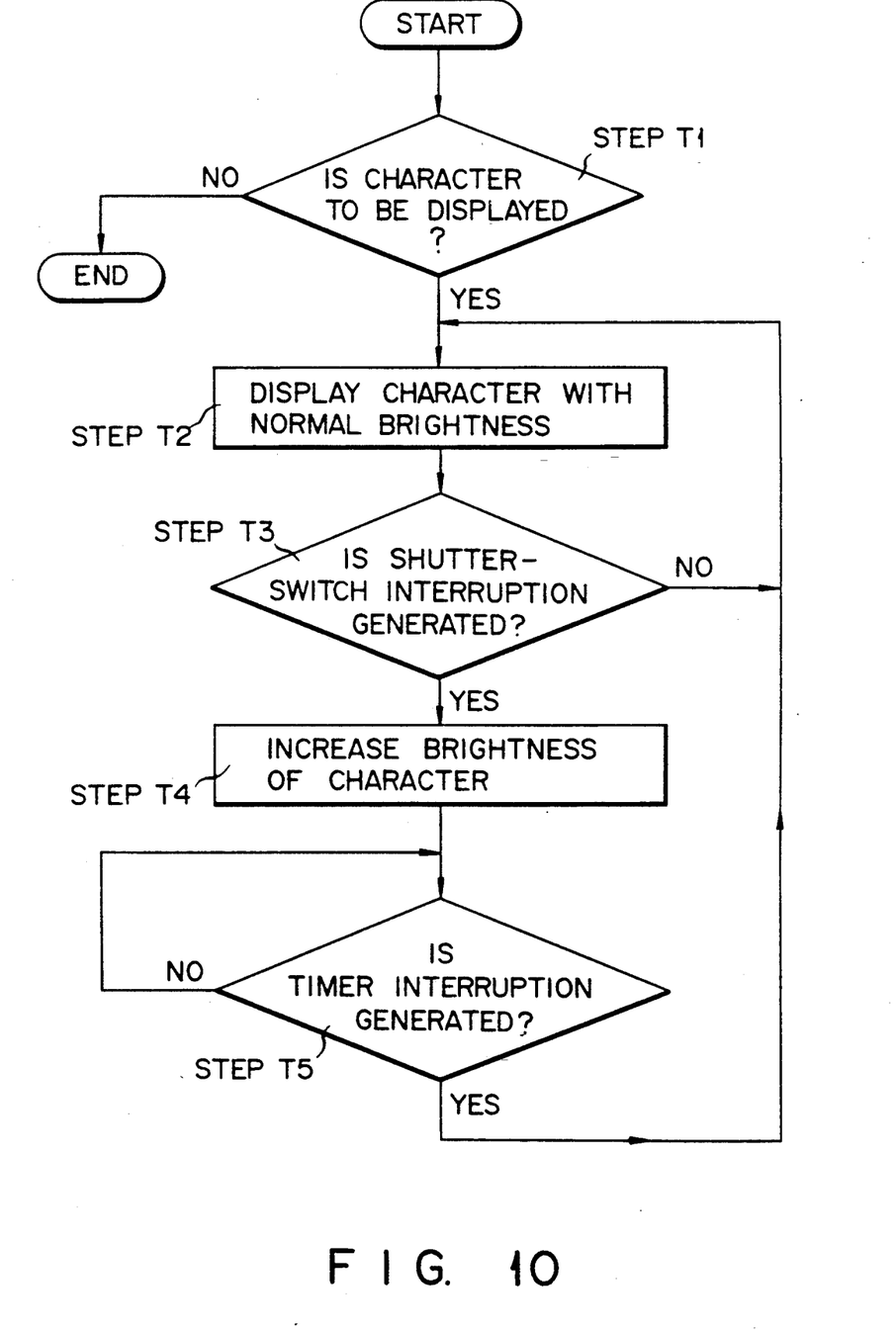
FIG. 10 is a flowchart illustrating the change of the state in the second display system in detail.

The state transition described above will be understood more clearly by referring to FIG. 10. As shown, a decision is made, in step T1, as to whether or not the marker 208 is to be displayed. If not, the operation is terminated. If, on the other hand, the marker is to be displayed, the operation advances to step T2, whereby the marker is displayed in state A, that is, displayed with a normal brightness. In step T3, when no shutter-switch interruption is generated, state A is maintained. When a shutter-switch interruption is generated, the state transition from A to B occurs so that the brightness of the marker is increased in step T4. In step T5, a decision is made as to whether or not a timer interruption is generated. If not, state B is maintained. When the timer interruption is generated, the state transition from state B to state A occurs.

As a result, when a display image on the TV monitor 73 is recorded by the instant camera, the marker 208' can be displayed distinctly, as shown in FIG. 6B. Therefore, the position of the detection line on an M-mode image and the position of the sampling point on a D-mode image will be easily recognized when a photograph of the images is observed. On the other hand, when a photograph is not taken, the marker 208 is displayed with its brightness decreased, as shown in FIG. 6A. Therefore, the observation of ultrasonic images is only slightly affected by the marker. This is very useful in avoiding diagnostic errors and in improving the accuracy of diagnosis.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An ultrasonic diagnosis apparatus, comprising:
   ultrasonic image generating means, for transmitting ultrasonic waves to and receiving reflected ultrasonic waves from a subject under examination to generate a B-mode image, an M-mode image, a D-mode image, a BDF-mode image, and/or an MDF-mode image;
   auxiliary information means for generating auxiliary information indicating a specific portion of said subject under examination;
   display means for displaying said B-mode image, said M-mode image, said D-mode image, said BDF-mode image, and/or said MDF-mode image with said auxiliary information such that a display of said auxiliary information is superimposed upon and moveable with respect to a display of said B-mode image and/or said BDF-mode image; and
   control means for controlling an intensity of said display of said auxiliary information in response to a change in position of said auxiliary information.

2. An ultrasonic diagnosis apparatus, comprising:
   ultrasonic image generating means for transmitting ultrasonic waves to and receiving reflected ultrasonic waves from a subject under examination to generate a B-mode image, an M-mode image, a D-mode image, a BDF-mode image, and/or an MDF-mode image;
   auxiliary information means for generating auxiliary information indicating a specific portion of said subject under examination;
   display means for displaying said B-mode image, said M-mode image, said D-mode image, said BDF-mode image, and/or said MDF-mode image with said auxiliary information as a superimposed image such that a display of said auxiliary information is superimposed upon and moveable with respect to a display of said B-mode image and/or said BDF-mode image;
   camera means for photographing the display of said B-mode image, said M-mode image; said D-mode image, said BDF-mode image, and/or said MDF-mode image with said auxiliary information; and control means for controlling an intensity of said display of said auxiliary information in response to a shutter operation of said camera means.

3. The ultrasonic diagnosis apparatus according to claim 1 or 2, where said control means restores said intensity of said display of said auxiliary information after a predetermined period of time.

4. The ultrasonic diagnosis apparatus according to claim 1 or 2, wherein said auxiliary information comprises a marker for indicating said specific portion of said subject under examination.

5. The ultrasonic diagnosis apparatus according to claim 1 or 2, wherein said auxiliary information comprises a character for indicating an ultrasonic diagnostic condition of said apparatus.

6. The ultrasonic diagnosis apparatus according to claim 1 or 2, further comprising mixing means for mixing said B-mode image, said M-mode image; said D-mode image, said BDF-mode image, and/or said MDF mode image with said auxiliary information to produce said superimposed image.

7. The ultrasonic diagnosis apparatus according to claim 1 or 2, wherein said control means selectively controls said intensity of said display of said auxiliary information such that said display is conspicuous or non-conspicuous.

* * * * *